United States Patent
Pennoyer, IV et al.

(10) Patent No.: US 12,029,523 B2
(45) Date of Patent: Jul. 9, 2024

(54) DRAPE MANAGEMENT ASSEMBLY FOR ROBOTIC SURGICAL SYSTEMS

(71) Applicant: Covidien LP, Mansfield, MA (US)

(72) Inventors: Raymond P. Pennoyer, IV, Berlin, CT (US); Chi Min Seow, New Haven, CT (US); Jaimeen Kapadia, Cambridge, MA (US); Shane Reardon, Branford, CT (US); Mark Hamilton MacLeod, Southbury, CT (US); Michael Zemlok, Prospect, CT (US)

(73) Assignee: COVIDIEN LP, Mansfield, MA (US)

( * ) Notice: Subject to any disclaimer, the term of this patent is extended or adjusted under 35 U.S.C. 154(b) by 889 days.

(21) Appl. No.: 16/767,380

(22) PCT Filed: Nov. 28, 2018

(86) PCT No.: PCT/US2018/062707
§ 371 (c)(1),
(2) Date: May 27, 2020

(87) PCT Pub. No.: WO2019/108567
PCT Pub. Date: Jun. 6, 2019

(65) Prior Publication Data
US 2020/0390511 A1    Dec. 17, 2020

Related U.S. Application Data

(60) Provisional application No. 62/593,308, filed on Dec. 1, 2017.

(51) Int. Cl.
*A61B 46/10* (2016.01)
*A61B 1/00* (2006.01)
(Continued)

(52) U.S. Cl.
CPC .......... *A61B 46/10* (2016.02); *A61B 1/00142* (2013.01); *A61B 34/30* (2016.02);
(Continued)

(58) Field of Classification Search
CPC ..... A61B 1/00142; A61B 34/30; A61B 46/10; A61B 50/00; A61B 50/30; A61B 90/57
See application file for complete search history.

(56) References Cited

U.S. PATENT DOCUMENTS

| 3,528,720 A | 9/1970 | Treace |
| 3,540,441 A | 11/1970 | Collins |

(Continued)

FOREIGN PATENT DOCUMENTS

| CN | 201440675 U | 4/2010 |
| CN | 202507720 U | 10/2012 |

(Continued)

OTHER PUBLICATIONS

Chinese First Office Action dated Nov. 16, 2022 corresponding to counterpart Patent Application CN 201880077534.0.

(Continued)

*Primary Examiner* — Scott Luan
(74) *Attorney, Agent, or Firm* — Carter, DeLuca & Farrell, LLP

(57) ABSTRACT

A drape management assembly for a robotic surgical system includes a clip having a base portion configured for selective connection to the robotic surgical system and a grasping portion extending from the base portion. The base portion and the grasping portion may define a cavity therebetween. The base portion and the grasping portion may be arranged to retain a quantity of a surgical drape in the cavity to minimize an excess quantity of a surgical drape sheathed over a robotic arm of the robotic surgical system.

13 Claims, 8 Drawing Sheets

(51) Int. Cl.
  *A61B 34/30*   (2016.01)
  *A61B 50/00*   (2016.01)
  *A61B 50/30*   (2016.01)
  *A61B 90/57*   (2016.01)
  *B25J 18/00*   (2006.01)

(52) U.S. Cl.
  CPC .............. *A61B 50/00* (2016.02); *A61B 50/30* (2016.02); *A61B 90/57* (2016.02); *B25J 18/00* (2013.01)

(56) References Cited

U.S. PATENT DOCUMENTS

| | | | |
|---|---|---|---|
| 3,707,964 A | 1/1973 | Patience et al. | |
| 3,747,655 A | 7/1973 | Hadtke | |
| 3,777,749 A | 12/1973 | Collins | |
| 3,952,738 A | 4/1976 | Krzewinski | |
| 3,955,569 A | 5/1976 | Krzewinski et al. | |
| 4,457,026 A | 7/1984 | Morris | |
| 4,919,112 A | 4/1990 | Siegmund | |
| 5,515,868 A | 5/1996 | Mills | |
| 5,522,403 A | 6/1996 | Bark et al. | |
| 5,740,699 A | 4/1998 | Ballantyne et al. | |
| 5,860,420 A | 1/1999 | Wiedner et al. | |
| 6,105,578 A | 8/2000 | Sommers et al. | |
| 6,116,741 A | 9/2000 | Paschal | |
| 6,123,080 A | 9/2000 | Mohan et al. | |
| 6,132,368 A | 10/2000 | Cooper | |
| 6,206,903 B1 | 3/2001 | Ramans | |
| 6,246,200 B1 | 6/2001 | Blumenkranz et al. | |
| 6,312,435 B1 | 11/2001 | Wallace et al. | |
| 6,331,181 B1 | 12/2001 | Tierney et al. | |
| 6,346,072 B1 | 2/2002 | Cooper | |
| 6,394,998 B1 | 5/2002 | Wallace et al. | |
| 6,424,885 B1 | 7/2002 | Niemeyer et al. | |
| 6,441,577 B2 | 8/2002 | Blumenkranz et al. | |
| 6,459,926 B1 | 10/2002 | Nowlin et al. | |
| 6,491,691 B1 | 12/2002 | Morley et al. | |
| 6,491,701 B2 | 12/2002 | Tierney et al. | |
| 6,493,608 B1 | 12/2002 | Niemeyer | |
| 6,565,554 B1 | 5/2003 | Niemeyer | |
| 6,645,196 B1 | 11/2003 | Nixon et al. | |
| 6,659,939 B2 | 12/2003 | Moll et al. | |
| 6,671,581 B2 | 12/2003 | Niemeyer et al. | |
| 6,676,684 B1 | 1/2004 | Morley et al. | |
| 6,685,698 B2 | 2/2004 | Morley et al. | |
| 6,699,235 B2 | 3/2004 | Wallace et al. | |
| 6,714,839 B2 | 3/2004 | Salisbury, Jr. et al. | |
| 6,716,233 B1 | 4/2004 | Whitman | |
| 6,728,599 B2 | 4/2004 | Wang et al. | |
| 6,746,443 B1 | 6/2004 | Morley et al. | |
| 6,766,204 B2 | 7/2004 | Niemeyer et al. | |
| 6,770,081 B1 | 8/2004 | Cooper et al. | |
| 6,772,053 B2 | 8/2004 | Niemeyer | |
| 6,783,524 B2 | 8/2004 | Anderson et al. | |
| 6,793,652 B1 | 9/2004 | Whitman et al. | |
| 6,793,653 B2 | 9/2004 | Sanchez et al. | |
| 6,799,065 B1 | 9/2004 | Niemeyer | |
| 6,837,883 B2 | 1/2005 | Moll et al. | |
| 6,839,612 B2 | 1/2005 | Sanchez et al. | |
| 6,840,938 B1 | 1/2005 | Morley et al. | |
| 6,843,403 B2 | 1/2005 | Whitman | |
| 6,846,309 B2 | 1/2005 | Whitman et al. | |
| 6,866,671 B2 | 3/2005 | Tierney et al. | |
| 6,871,117 B2 | 3/2005 | Wang et al. | |
| 6,879,880 B2 | 4/2005 | Nowlin et al. | |
| 6,899,705 B2 | 5/2005 | Niemeyer | |
| 6,902,560 B1 | 6/2005 | Morley et al. | |
| 6,923,186 B2 | 8/2005 | Gavette et al. | |
| 6,936,042 B2 | 8/2005 | Wallace et al. | |
| 6,951,535 B2 | 10/2005 | Ghodoussi et al. | |
| 6,974,449 B2 | 12/2005 | Niemeyer | |
| 6,991,627 B2 | 1/2006 | Madhani et al. | |
| 6,994,708 B2 | 2/2006 | Manzo | |
| 7,025,064 B2 | 4/2006 | Wang et al. | |
| 7,048,745 B2 | 5/2006 | Tierney et al. | |
| 7,066,926 B2 | 6/2006 | Wallace et al. | |
| 7,118,582 B1 | 10/2006 | Wang et al. | |
| 7,125,403 B2 | 10/2006 | Julian et al. | |
| 7,155,315 B2 | 12/2006 | Niemeyer et al. | |
| 7,239,940 B2 | 7/2007 | Wang et al. | |
| 7,306,597 B2 | 12/2007 | Manzo | |
| 7,357,774 B2 | 4/2008 | Cooper | |
| 7,373,219 B2 | 5/2008 | Nowlin et al. | |
| 7,379,790 B2 | 5/2008 | Toth et al. | |
| 7,386,365 B2 | 6/2008 | Nixon | |
| 7,391,173 B2 | 6/2008 | Schena | |
| 7,398,707 B2 | 7/2008 | Morley et al. | |
| 7,413,565 B2 | 8/2008 | Wang et al. | |
| 7,453,227 B2 | 11/2008 | Prisco et al. | |
| 7,524,320 B2 | 4/2009 | Tierney et al. | |
| 7,574,250 B2 | 8/2009 | Niemeyer | |
| 7,594,912 B2 | 9/2009 | Cooper et al. | |
| 7,607,440 B2 | 10/2009 | Coste-Maniere et al. | |
| 7,666,191 B2 | 2/2010 | Orban, III et al. | |
| 7,682,357 B2 | 3/2010 | Ghodoussi et al. | |
| 7,689,320 B2 | 3/2010 | Prisco et al. | |
| 7,695,481 B2 | 4/2010 | Wang et al. | |
| 7,695,485 B2 | 4/2010 | Whitman et al. | |
| 7,699,855 B2 | 4/2010 | Anderson et al. | |
| 7,713,263 B2 | 5/2010 | Niemeyer | |
| 7,725,214 B2 | 5/2010 | Diolaiti | |
| 7,727,244 B2 | 6/2010 | Orban, III et al. | |
| 7,741,802 B2 | 6/2010 | Prisco et al. | |
| 7,756,036 B2 | 7/2010 | Druke et al. | |
| 7,757,028 B2 | 7/2010 | Druke et al. | |
| 7,762,825 B2 | 7/2010 | Burbank et al. | |
| 7,778,733 B2 | 8/2010 | Nowlin et al. | |
| 7,803,151 B2 | 9/2010 | Whitman | |
| 7,806,891 B2 | 10/2010 | Nowlin et al. | |
| 7,819,859 B2 | 10/2010 | Prisco et al. | |
| 7,819,885 B2 | 10/2010 | Cooper | |
| 7,824,401 B2 | 11/2010 | Manzo et al. | |
| 7,835,823 B2 | 11/2010 | Sillman et al. | |
| 7,843,158 B2 | 11/2010 | Prisco | |
| 7,865,266 B2 | 1/2011 | Moll et al. | |
| 7,865,269 B2 | 1/2011 | Prisco et al. | |
| 7,886,743 B2 | 2/2011 | Cooper et al. | |
| 7,899,578 B2 | 3/2011 | Prisco et al. | |
| 7,907,166 B2 | 3/2011 | Lamprecht et al. | |
| 7,935,130 B2 | 5/2011 | Williams | |
| 7,963,913 B2 | 6/2011 | Devengenzo et al. | |
| 7,983,793 B2 | 7/2011 | Toth et al. | |
| 7,992,560 B2 | 8/2011 | Burton et al. | |
| 8,002,767 B2 | 8/2011 | Sanchez et al. | |
| 8,004,229 B2 | 8/2011 | Nowlin et al. | |
| 8,012,170 B2 | 9/2011 | Whitman et al. | |
| 8,054,752 B2 | 11/2011 | Druke et al. | |
| 8,062,288 B2 | 11/2011 | Cooper et al. | |
| 8,079,950 B2 | 12/2011 | Stern et al. | |
| 8,100,133 B2 | 1/2012 | Mintz et al. | |
| 8,108,072 B2 | 1/2012 | Zhao et al. | |
| 8,120,301 B2 | 2/2012 | Goldberg et al. | |
| 8,142,447 B2 | 3/2012 | Cooper et al. | |
| 8,147,503 B2 | 4/2012 | Zhao et al. | |
| 8,151,661 B2 | 4/2012 | Schena et al. | |
| 8,155,479 B2 | 4/2012 | Hoffman et al. | |
| 8,182,469 B2 | 5/2012 | Anderson et al. | |
| 8,202,278 B2 | 6/2012 | Orban, III et al. | |
| 8,206,406 B2 | 6/2012 | Orban, III | |
| 8,210,413 B2 | 7/2012 | Whitman et al. | |
| 8,216,250 B2 | 7/2012 | Orban, III et al. | |
| 8,220,468 B2 | 7/2012 | Cooper et al. | |
| 8,256,319 B2 | 9/2012 | Cooper et al. | |
| 8,285,517 B2 | 10/2012 | Sillman et al. | |
| 8,315,720 B2 | 11/2012 | Mohr et al. | |
| 8,335,590 B2 | 12/2012 | Costa et al. | |
| 8,347,757 B2 | 1/2013 | Duval | |
| 8,374,723 B2 | 2/2013 | Zhao et al. | |
| 8,418,073 B2 | 4/2013 | Mohr et al. | |
| 8,419,717 B2 | 4/2013 | Diolaiti et al. | |
| 8,423,182 B2 | 4/2013 | Robinson et al. | |
| 8,452,447 B2 | 5/2013 | Nixon | |
| 8,454,585 B2 | 6/2013 | Whitman | |

(56) References Cited

U.S. PATENT DOCUMENTS

| | | |
|---|---|---|
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,813,755 B2 | 8/2014 | Hoffmann |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,828,023 B2 | 9/2014 | Neff et al. |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart et al. |
| 8,989,903 B2 | 3/2015 | Weir et al. |
| 9,002,518 B2 | 4/2015 | Manzo et al. |
| 9,014,856 B2 | 4/2015 | Manzo et al. |
| 9,016,540 B2 | 4/2015 | Whitman et al. |
| 9,019,345 B2 | 4/2015 | O |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti et al. |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,629,680 B2 | 4/2017 | Winer |
| 9,662,177 B2 | 5/2017 | Weir et al. |
| 9,664,262 B2 | 5/2017 | Donlon et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin et al. |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |

(56) References Cited

U.S. PATENT DOCUMENTS

| | | |
|---|---|---|
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | McDonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |
| 2003/0106493 A1 | 6/2003 | Christian et al. |
| 2006/0161138 A1 | 7/2006 | Orban et al. |
| 2006/0199999 A1 | 9/2006 | Keda et al. |
| 2008/0065105 A1 | 3/2008 | Larkin et al. |
| 2009/0248039 A1 | 10/2009 | Cooper et al. |
| 2011/0041995 A1 | 2/2011 | Adams |
| 2011/0259347 A1 | 10/2011 | Zurn |
| 2015/0047647 A1 | 2/2015 | Winer |
| 2015/0096475 A1 | 4/2015 | Lee et al. |
| 2015/0374445 A1 | 12/2015 | Gombert et al. |
| 2017/0086934 A1* | 3/2017 | Devengenzo .......... A61B 46/23 |
| 2020/0093556 A1 | 3/2020 | Zemlok et al. |

FOREIGN PATENT DOCUMENTS

| | | | |
|---|---|---|---|
| JP | 2012106440 A | | 6/2012 |
| KR | 20120014275 | * | 2/2012 |
| KR | 20120014275 A | | 2/2012 |
| KR | 101113980 B1 | | 3/2012 |
| WO | 8501496 A1 | | 4/1985 |
| WO | 9832391 A1 | | 7/1998 |
| WO | 2015142824 A1 | | 9/2015 |
| WO | 2017147350 A1 | | 8/2017 |

OTHER PUBLICATIONS

Vertut, Jean and Philippe Coiffet, Teleoperation and Robotics: Evolution and Development, English translation Prentice-Hall, Inc., Inglewood Cliffs, NJ, USA, 1986 (Abstract Only).

International Search Report dated Mar. 20, 2019, corresponding to International Application No. PCT/US2018/062707; 2 pages.

European Search Report dated Jul. 22, 2021, issued in corresponding EP Appln. No. 18883997, 7 pages.

* cited by examiner

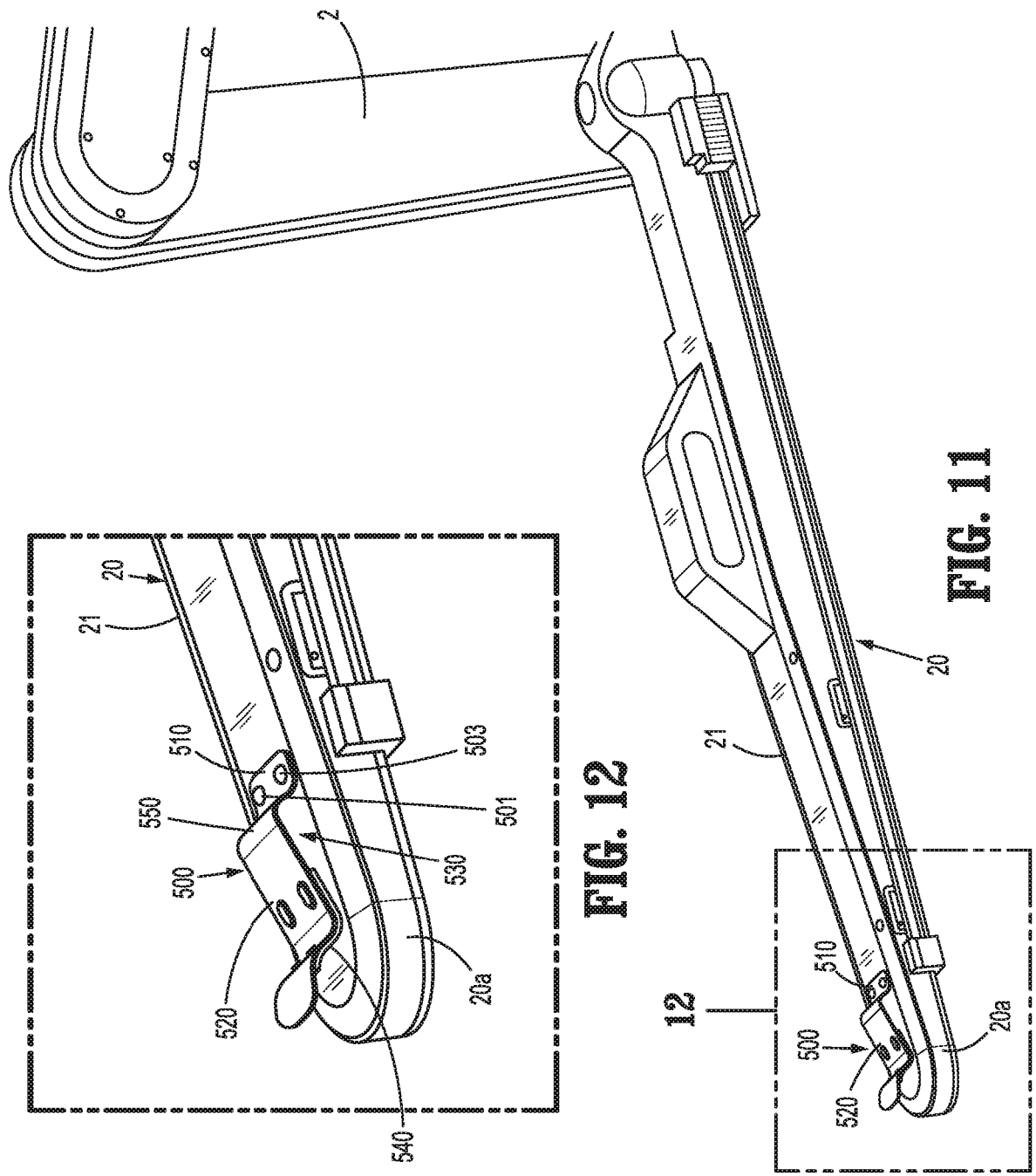

DRAPE MANAGEMENT ASSEMBLY FOR ROBOTIC SURGICAL SYSTEMS

CROSS-REFERENCE TO RELATED APPLICATIONS

This application is a U.S. National Stage Application filed under 35 U.S.C. § 371(a) of International Patent Application Serial No. PCT/US2018/062707, filed Nov. 28, 2018, which claims the benefit of and priority to U.S. Provisional Patent Application Ser. No. 62/593,308, filed Dec. 1, 2017, the entire disclosure of which is incorporated by reference herein.

BACKGROUND

Robotic surgical systems have been used in minimally invasive medical procedures. Some robotic surgical systems include a console supporting a robotic arm, and a robotic surgical instrument having at least one end effector (e.g., forceps or a grasping tool) mounted to the robotic arm via a wrist assembly. In some systems, cables extend from the console, through the robotic arm, and connect to the wrist assembly and/or end effector to provide mechanical power to the end effector for its operation and movement.

During a medical procedure, the end effector and the wrist assembly are inserted into a small incision (via a cannula) or a natural orifice of a patient to position the end effector at a work site within the body of the patient. In order to establish and maintain a sterile barrier between the patient, a surgical field, and/or the robotic surgical system, a drape may be used to enclose or sheath a portion of the robotic surgical system.

However, it is often the case that excess draping material may interfere with the medical procedure by interfering with a movement of the robotic arm or robotic surgical instrument and/or getting in the way of medical personnel.

Accordingly, a need exists for a way to contain excess draping material during a medical procedure.

SUMMARY

The present disclosure relates to robotics surgical systems, and more specifically, to drape management assemblies for robotic assisted surgery.

According to an aspect of the present disclosure, a drape management assembly for a robotic surgical system is provided, including a clip having a base portion configured for selective connection to the robotic surgical system and a grasping portion extending from the base portion. The base portion and the grasping portion may define a cavity therebetween. The base portion and the grasping portion may be arranged to retain a quantity of a surgical drape in the cavity to minimize an excess quantity of a surgical drape sheathed over a robotic arm of the robotic surgical system.

In embodiments, each of the base portion and the grasping portion may define a first axis, the first axis of the base portion and the first axis of the grasping portion being at an angle relative to each other.

In other embodiments, a distal end portion of the grasping portion may define a lip having a second axis that may be at an angle relative to the first axis of the grasping portion.

In yet other embodiments, a tab may extend from the lip of the grasping portion, the tab defining a third axis that may be at an angle relative to the second axis of the lip.

In still yet other embodiments, the clip may include an insert configured to couple to the clip, the insert including a top surface having a plurality of protrusions extending therefrom. The plurality of protrusions may include a plurality of flanges extending from a surface thereof. The insert may include a frictional bottom surface configured for contact with a surgical drape, whereby a gripping of the surgical drape by the clip is enhanced.

In embodiments, a plurality of slots may be defined through the clip, the plurality of slots of the clip configured to receive the plurality of protrusions of the insert to couple the insert to the clip.

In other embodiments, when the insert is coupled to the clip, the clip may be disposed between a bottom surface of the plurality of flanges and the top surface of the insert.

In yet other embodiments, the clip may be coated from a material selecting from the group consisting of rubber and silicone.

In still yet other embodiments, the clip may be formed from a material selected from the group consisting of plastic, steel, stainless steel, spring steel. and sheet metal.

In embodiments, the clip may be plated with a material selected from the group consisting of electroless nickel, bright nickel, chrome, and zinc.

In other embodiments, the insert may be formed from a material selected from the group consisting of silicone, natural rubber, nitrile, and urethane.

In yet other embodiments, the clip may include an elbow interconnecting the base portion and the grasping portion, and the elbow may be configured to resiliently bias the grasping portion of the clip towards an approximated position.

In still yet other embodiments, the clip may be movable between an approximated position and an unapproximated position relative to the robotic surgical instrument.

According to another aspect of the present disclosure, a robotic surgical assembly may be provided including a robotic arm, a surgical drape, and a clip configured to couple the surgical drape to the robotic arm. The clip may include a base portion configured for selective connection to the robotic arm and a grasping portion extending from the base portion. The base portion and the grasping portion may define a cavity therebetween. The base portion and the grasping portion may be arranged to retain a quantity of the surgical drape in the cavity, whereby an excess quantity of the surgical drape sheathed over the robotic arm may be minimized.

The robotic surgical assembly may include an insert configured to couple to the clip. The insert may include a top surface having a plurality of protrusions extending therefrom. The plurality of protrusions may include a plurality of flanges extending from a surface thereof. The insert may include a frictional bottom surface configured for contact with a surgical drape, whereby a gripping of the surgical drape by the clip is enhanced.

In embodiments, a plurality of slots may be defined through the clip, the plurality of slots of the clip configured to receive the plurality of protrusions of the insert to couple the insert to the clip.

In other embodiments, the surgical drape may be configured to enclose the robotic arm, and the clip and the insert may be configured to incrementally release the excess quantity of the surgical drape such that the robotic arm maintains a full range of motion while enclosed within the surgical drape.

In yet other embodiments, the excess quantity of the surgical drape may be retained between an upper portion of an instrument drive unit and the clip or a slide rail and the clip. The slide rail may be connected to the robotic arm, and the instrument drive unit may be connected to the slide rail.

In still yet other embodiments, the clip may include an elbow interconnecting the base portion and the grasping portion, and the elbow may be configured to resiliently bias the grasping portion of the clip to an approximated position towards the instrument drive unit.

In embodiments, the clip may be formed from a material selected from the group consisting of plastic, steel, stainless steel, spring steel, and sheet metal.

In other embodiments, the base portion of the clip may be coupled to the instrument drive unit or the slide rail, and the grasping portion of the clip may be movable between an approximated position and an unapproximated position relative to the instrument drive unit or the slide rail.

BRIEF DESCRIPTION OF THE DRAWINGS

Embodiments of the present disclosure are described herein with reference to the accompanying drawings, wherein:

FIG. 11 is a perspective view of another embodiment of a clip, shown attached to an end portion of a slide rail of the robotic arm of FIG. 1; and FIG. 12 is an enlarged view, of the area of detail designated "12" in FIG. 11.

DETAILED DESCRIPTION

Figure 1:
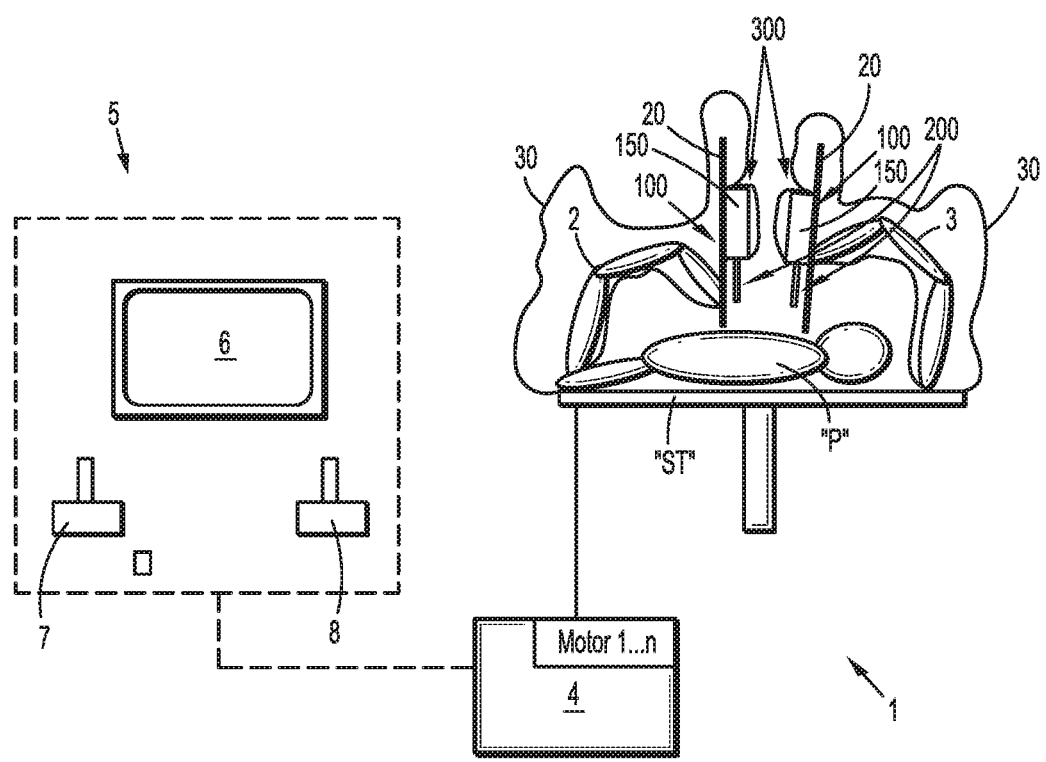
FIG. 1 is a schematic illustration of a robotic surgical system including a drape management assembly in accordance with the present disclosure.

Embodiments of the present disclosure will now be described in detail with reference to the drawings, in which like reference numerals designate identical or corresponding elements in each of the several views. As used herein, the term "clinician" refers to a doctor, nurse, or other care provider and may include support personnel. In the following description, well-known functions or constructions are not described in detail to avoid obscuring the present disclosure in unnecessary detail. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In the following description, well-known functions or constructions are not described in detail to avoid obscuring the present disclosure in unnecessary detail.

The present disclosure relates to surgical drape management assemblies. Specifically, the drape management assembly may be a clip including a base portion configured for selective connection to the robotic surgical system and a grasping portion extending from the base portion. The base portion and the grasping portion may define a cavity therebetween (when secured to an instrument drive unit of the robotic surgical system), wherein the base portion and the grasping portion are arranged to retain a quantity of a surgical drape in the cavity. The clip minimizes an excess quantity of a surgical drape sheathed over a robotic arm of the robotic surgical system.

Referring initially to FIG. 1, a surgical system, such as, for example, a robotic surgical system 1, generally includes one or more robotic arms 2, 3, a control device 4, and an operating console 5 coupled with control device 4. Robotic arms 2, 3 may each have a robotic surgical assembly 100 and an electromechanical surgical instrument 200 coupled thereto. In some embodiments, robotic surgical assembly 100 may be coupled to an end portion 20a of a slide rail 20 of robotic arms 2, 3.

Operating console 5 includes a display device 6, which is set up to display three-dimensional images, and manual input devices 7, 8, by means of which a clinician (not shown), is able to telemanipulate robotic arms 2, 3 in a first operating mode, as known in principle to a person skilled in the art. Robotic arms 2, 3 may be driven by electric drives (not shown) that are connected to control device 4 (e.g., a computer) which is set up to activate the drives, for example, by means of a computer program, in such a way that robotic arms 2, 3, the attached robotic surgical assembly 100, and thus electromechanical surgical instrument 200 (including the electromechanical end effector, not shown) execute a desired movement according to a movement defined by means of manual input devices 7, 8. Control device 4 may also be set up such that it regulates the movement of robotic arms 2, 3 and/or of the electric drives. To that end, control device 4 may control a plurality of motors, e.g., motors (Motor 1 . . . n), with each motor configured to drive movement of robotic arms 2, 3 in a plurality of directions.

Robotic surgical system 1 is configured for use on a patient "P" positioned (e.g., lying) on a surgical table "ST" to be treated in a minimally invasive manner by means of a surgical instrument, e.g., electromechanical surgical instrument 200. The robotic surgical system 1 may also include more than two robotic arms 2, 3, the additional robotic arms likewise connected to control device 4 and telemanipulatable by means of operating console 5. The robotic surgical assembly 100 may control an instrument drive unit 150 axially movable along the rail 20 of the robotic arms, 2, 3, and configured to drive various operations of an end effector (not explicitly shown) of the electromechanical surgical instrument 200, along a longitudinal axis "X" thereof.

For a detailed description of the construction and operation of a robotic surgical system, reference may be made to U.S. Pat. No. 8,828,023, the entire contents of which are incorporated by reference herein.

With continued reference to FIG. 1, robotic surgical system 1 includes one or more sterile barriers or drapes 30 enclosing or sheathing robotic arms 2, 3, instrument drive units 150, and robotic surgical assemblies 100 coupled thereto. Surgical drape 30 is configured to create an enclosed or protected sterile environment to prevent contamination of a surgical field from robotic arms 2, 3, robotic surgical assemblies 100, instrument drive units 150, and the like. It is envisioned that surgical drape 30 includes excess draping material or portions to provide enough slack such that the enclosed robotic arms 2, 3 and robotic surgical assemblies 100 coupled thereto remain operable in a full range of motion while remaining within the sterile enclosure of surgical drape 30 and without damaging or penetrating surgical drape 30.

Figure 3:
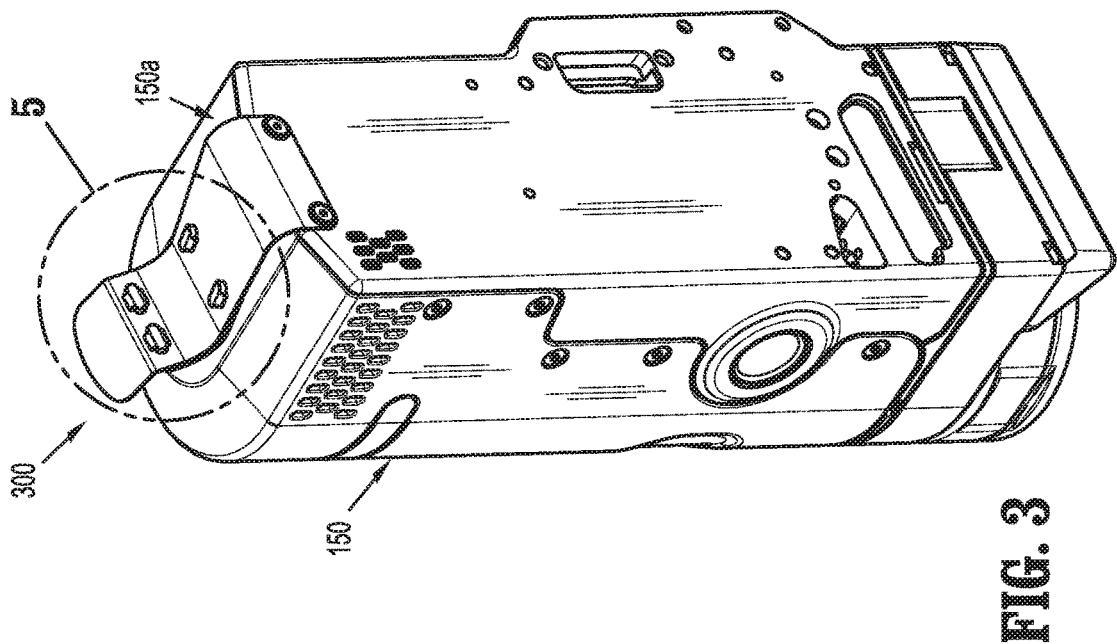
FIG. 3 is a rear, perspective view of the instrument drive unit and the drape management assembly of FIG. 2.
Figure 2:
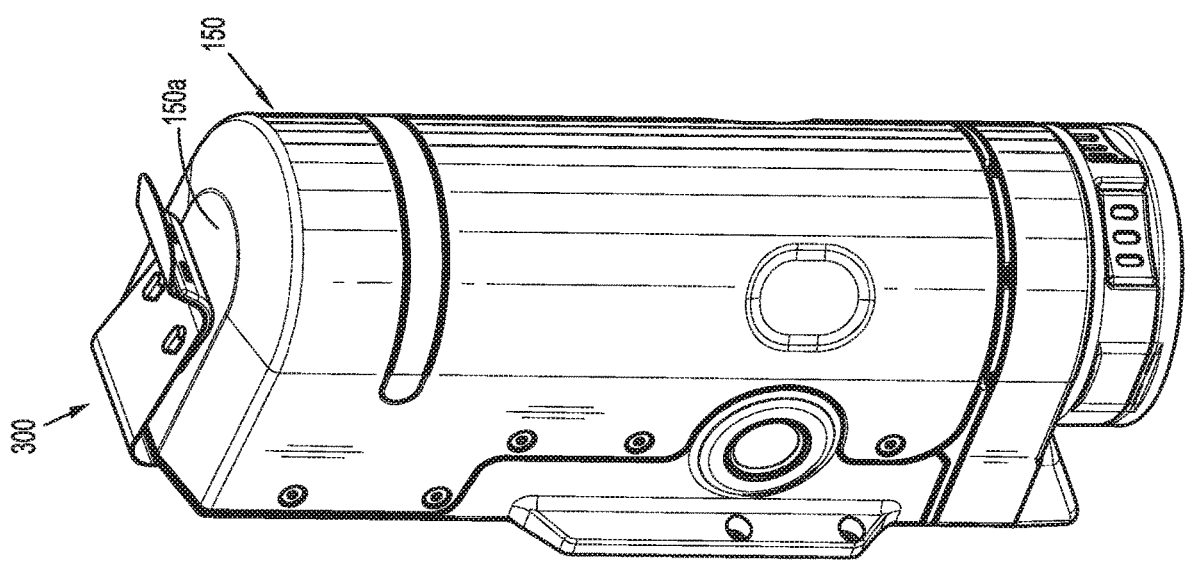
FIG. 2 is a front, perspective view of an instrument drive unit of the robotic surgical system and the drape management assembly attached thereto.
Figure 4:
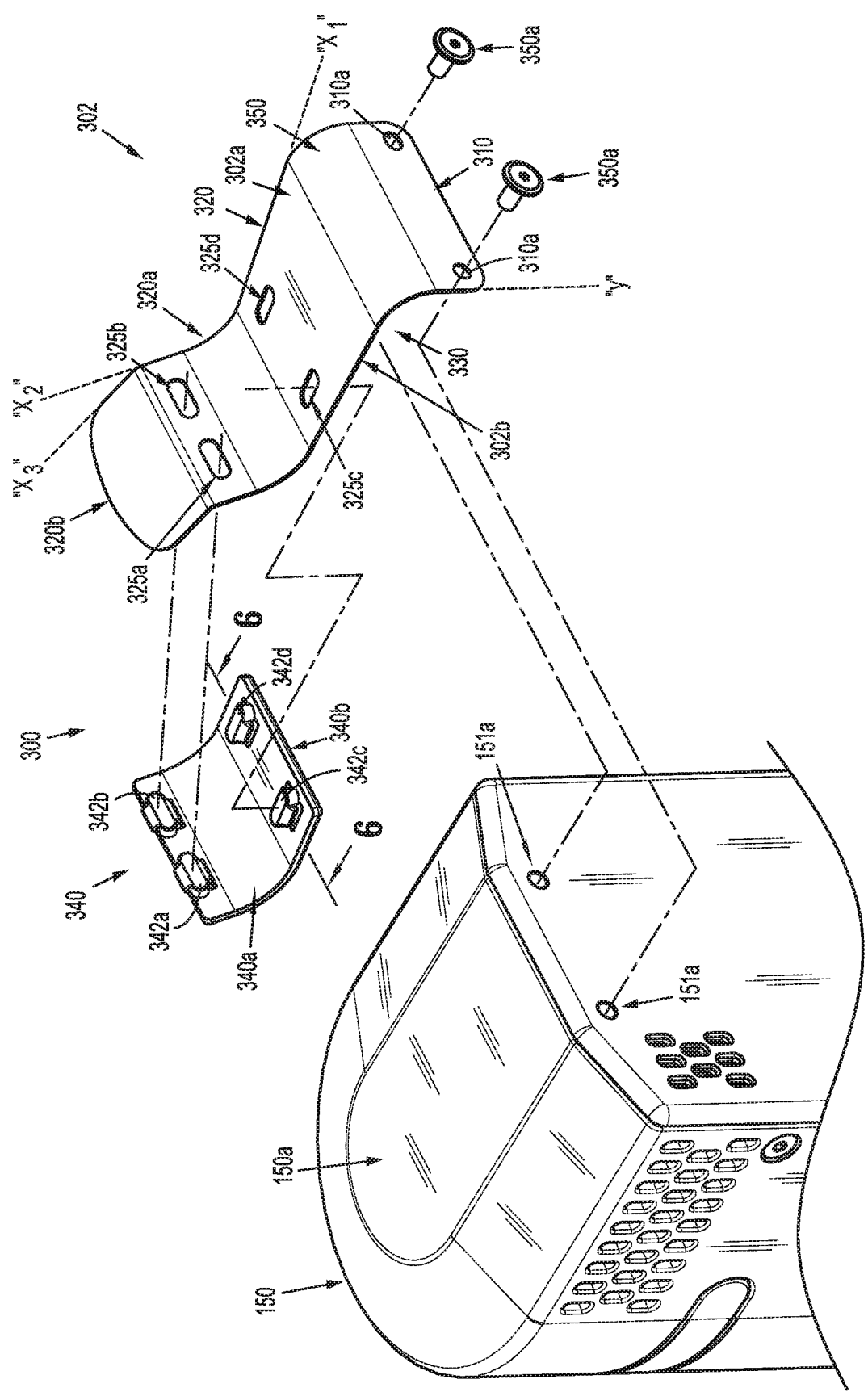
FIG. 4 is a perspective view, with parts separated, of the drape management assembly of FIGS. 2 and 3, and illustrating coupling of the drape management assembly to a rear, upper portion of the instrument drive unit.
Figure 5:
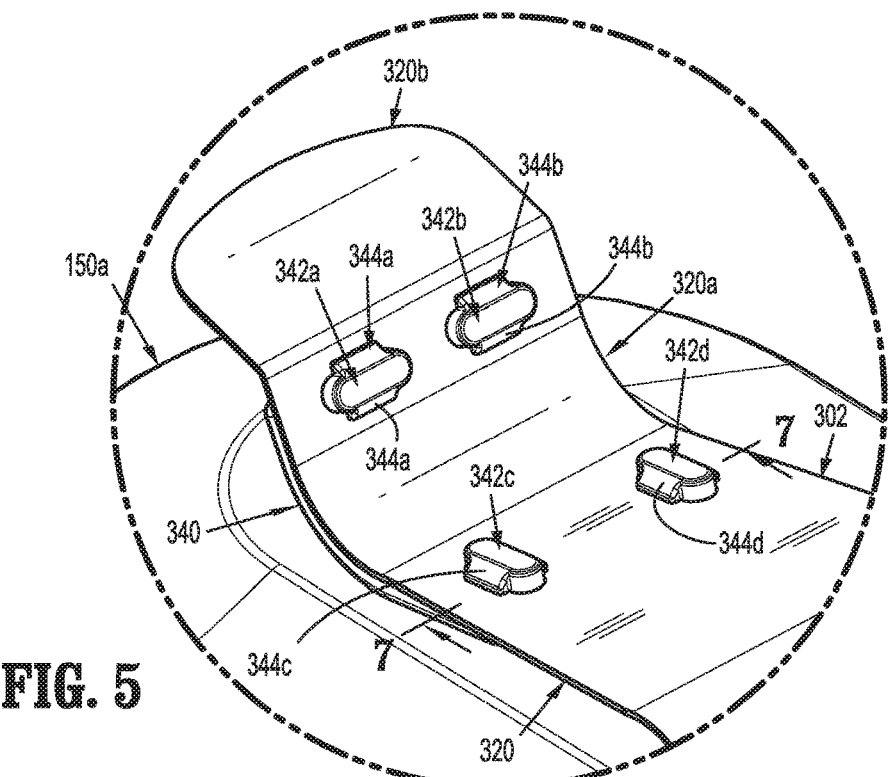
FIG. 5 is an enlarged view of the indicated area of detail delineated in FIG. 3.
Figure 6:
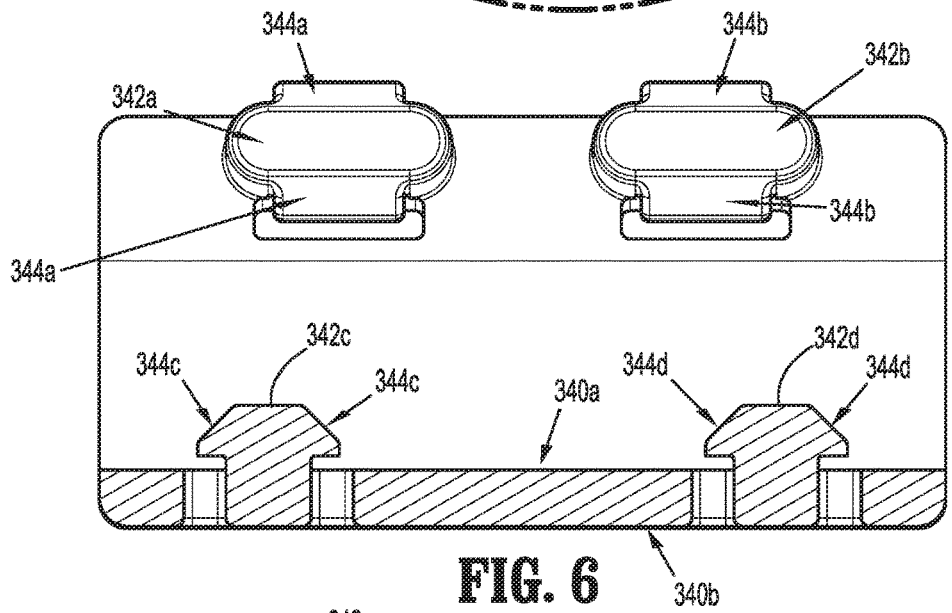
FIG. 6 is a cross-sectional view of an insert of the drape management assembly of FIG. 4 taken along the line 6-6 thereof.
Figure 8:
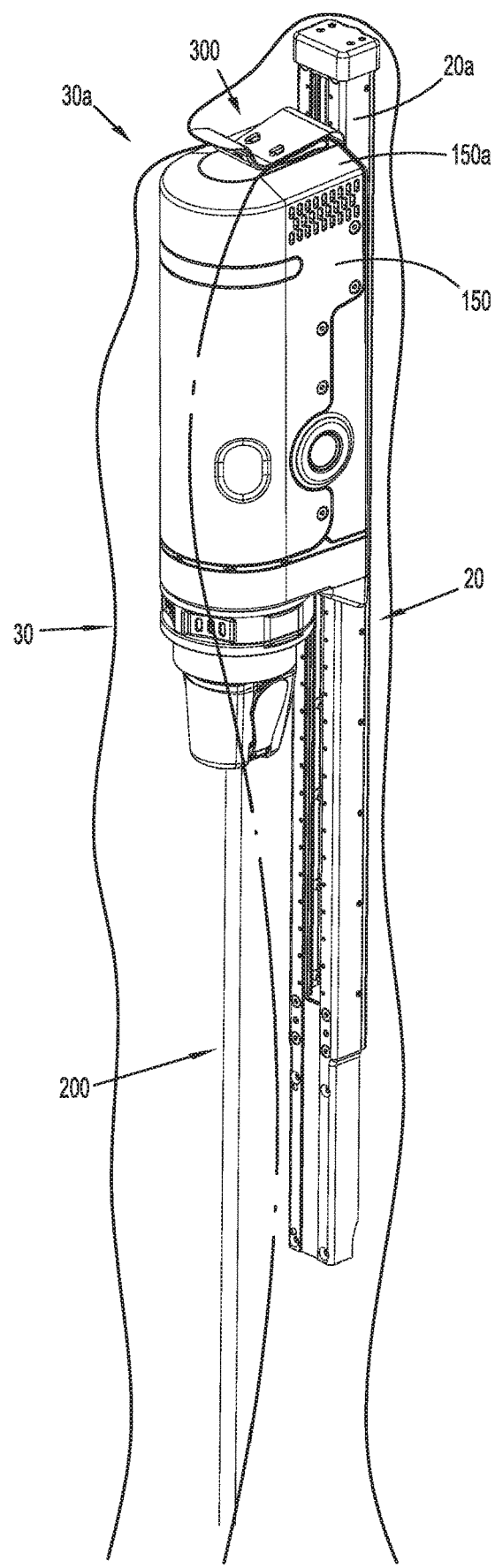
FIG. 8 is a front, perspective view of the drape management assembly positioned on a slide rail of a robotic arm and including a surgical drape sheathing the slide rail of the robotic arm.
Figure 9:
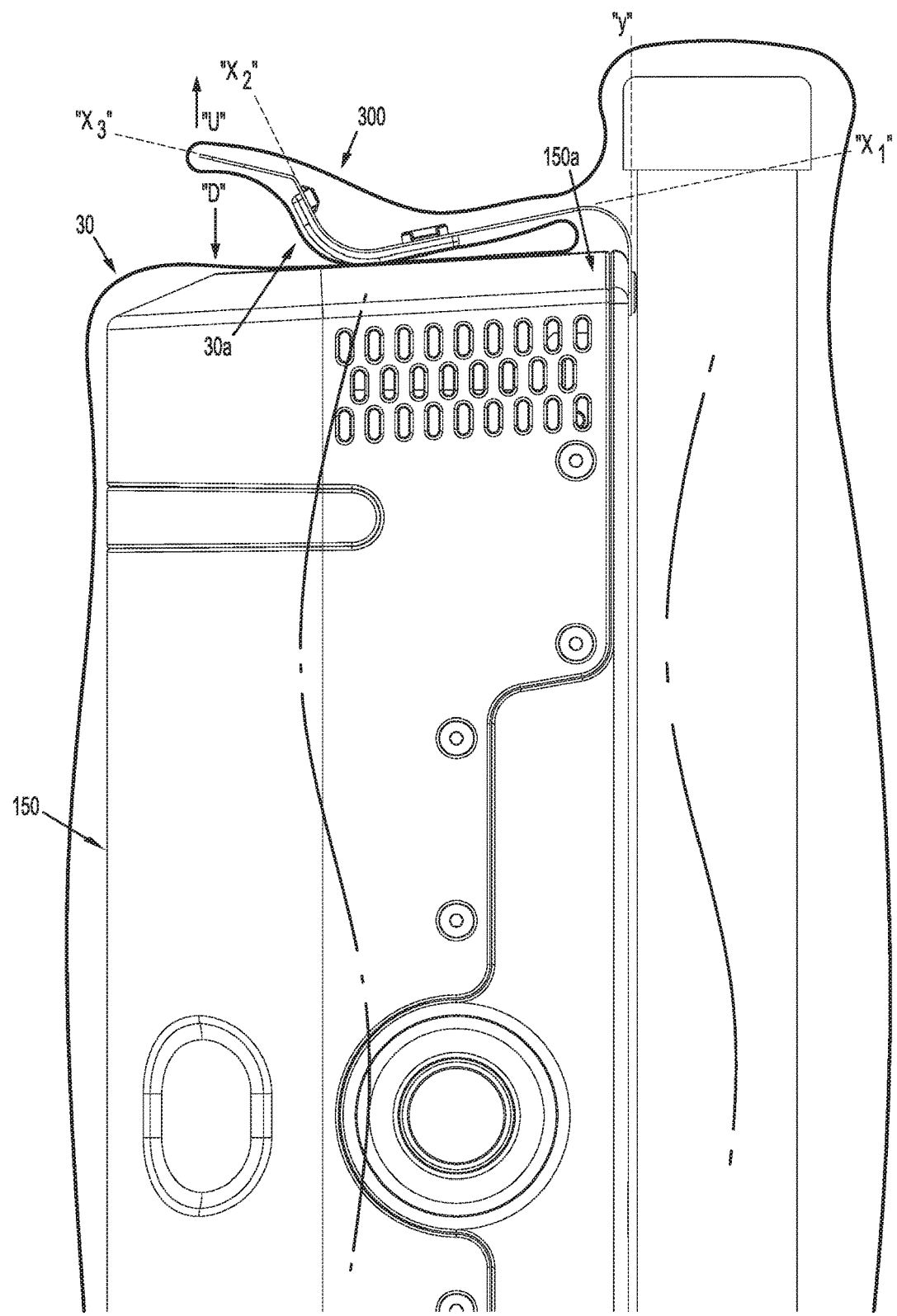
FIG. 9 is a partial, side view of the drape management assembly of FIG. 8.

With reference to FIGS. 2, 3 and 4, robotic surgical system 1 includes a drape management assembly 300 configured to control and manage the excess draping material, such as, for example, an excess quantity 30a of surgical drape 30 (FIGS. 1, 8, and 9). In embodiments, drape management assembly 300 is operably coupled to an upper portion 150a of the instrument drive unit 150. However, it is contemplated that drape management assembly 300 may be coupled to any surface of instrument drive unit 150, or to alternative or additional components of robotic surgical system 1 (not specifically shown).

With reference to FIG. 4, drape management assembly 300 may generally include a clip 302 having a top surface 302a, a bottom surface 302b, a base portion 310 configured for selective connection to the instrument drive unit 150, and a grasping portion 320 extending from the base portion 310 for affixing or pinning the surgical drape 30 to the instrument drive unit 150.

The base portion 310 of the clip 302 may define apertures 310a, which are configured to align with apertures 151a of the upper portion 150a of the instrument drive unit 150. Fasteners 350a of the drape management assembly 300 are configured to be inserted through apertures 310a of the base portion 310 of the clip 302 and through apertures 151a of the instrument drive unit 150 to affix the clip 302 to the upper portion 150a of the instrument drive unit 150, as shown in FIG. 3. In embodiments, the drape management assembly 300 may utilize any number of apertures 310a or fasteners 350a to couple to a surface of the robotic surgical assembly 100. In certain embodiments, fasteners 350a may be, and not limited to, screws, bolts, pins, dowels, buttons, rivets, etc.

With reference to FIGS. 4 and 9, the base portion 310 of the clip 302 may define an axis "Y." The grasping portion 320 of the clip 302 may define a first axis "$X_1$" that may be oriented at an angle (e.g., an acute angle) relative to axis "Y" of the base portion 310. A distal end portion of the grasping portion 320 of the clip 302 may include a lip 320a extending therefrom. The lip 320a of the grasping portion 320 of the clip 302 may define a second axis "$X_2$" that may be oriented at an angle (e.g., an obtuse angle) relative to the first axis "$X_1$" of the grasping portion 320. The grasping portion 320 of the clip 302 may further define a tab 320b extending distally of the lip 320a, and may be configured for lifting or otherwise moving the clip 302 when it is coupled to the instrument drive unit 150 for placement of a surgical drape 30 between instrument drive unit 150 and clip 302. The tab 320b of the clip 302 may define a third axis "$X_3$" that may be oriented at an angle relative to the first and second axes "$X_1$" and "$X_2$" of the grasping portion 320 of the clip 302.

Any suitable angle between the respective axes "Y," "$X_1$," "$X_2$," and "$X_3$" is contemplated. For example, the angle between axis "Y" of base portion 310 and axis "$X_1$" of grasping portion 320 may be from about 60 to about 90 degrees, and the angle between axis "$X_1$" of grasping portion 320 and axis "$X_2$" of lip 320a may be from about 80 to about 120 degrees. In embodiments, the angle between axis "Y" of base portion 310 and axis "$X_1$" of grasping portion 320 may be from about 65 to about 75 degrees (e.g., about 71 degrees), and the angle between axis "$X_1$" of grasping portion 320 and axis "$X_2$" of lip 320a may be from about 90 to about 110 degrees (e.g., about 105 degrees).

The base portion 310 and the grasping portion 320 of the clip 302, together with outer surfaces of instrument drive unit 150, may define a cavity or gap 330 therebetween, wherein the base portion 310 and the grasping portion 320 are arranged to retain a quantity of the surgical drape 30 in the cavity or gap 330 of the drape management assembly 300. As such, the drape management assembly 300 minimizes, reduces, or otherwise eliminates an excess quantity 30a (FIGS. 8 and 9) of the surgical drape 30 sheathed over robotic arms 2, 3, of the robotic surgical system 1. In embodiments, the drape management assembly 300 may be configured to incrementally release the excess quantity 30a as necessary to maintain a full range of the robotic arms 2, 3 and the robotic surgical assemblies 100 coupled thereto while remaining within the enclosure of the surgical drape 30. For example, the movement of robotic arms 2, 3 and the robotic surgical assemblies 100 causes a gradual or incremental release of excess quantity 30a of surgical drape 30 from the cavity or gap 330 of clip 302. As the robotic arms 2, 3 and the robotic surgical assemblies 100 move or are otherwise actuated, only the excess quantity 30a necessary for adequately enclosing or sheathing the robotic arms 2, 3 and the robotic surgical assemblies 100 is released from drape management assembly 300, while simultaneously permitting the robotic arms 2, 3 and the robotic surgical assemblies 100 to maintain a full range of motion.

The grasping portion 320 of clip 302 may further define a plurality of slots 325a-325d extending therethrough. In embodiments, a longitudinal axis of slots 325a, 325b may be disposed 90 degrees relative to a longitudinal axis of slots 325c, 325d.

The drape management assembly 300 may further include an insert 340 configured to selectively couple with the clip 302. The insert 340 may be used, e.g., to enhance the ability of the clip 302 to grip the surgical drape 30, and/or the excess quantity 30a of the surgical drape 30. The insert 340 of the drape management assembly 300 includes a top surface 340a and a bottom surface 340b. Insert 340 includes a plurality of protrusions 342a-342d extending therefrom configured to selectively engage the respective slots 325a-325d, of the clip 302. The plurality of protrusions 342a-342d of the insert 340 may further define respective flanges 344a-344d, which extend outwardly from a surface of the protrusions 342a-342d of the insert 340 of the drape management assembly 300. In embodiments, protrusions 342a, 342b of the insert 340 may have a longitudinal axis disposed 90 degrees relative to a longitudinal axis of slots 325a, 325b of clip 302.

Figure 7:
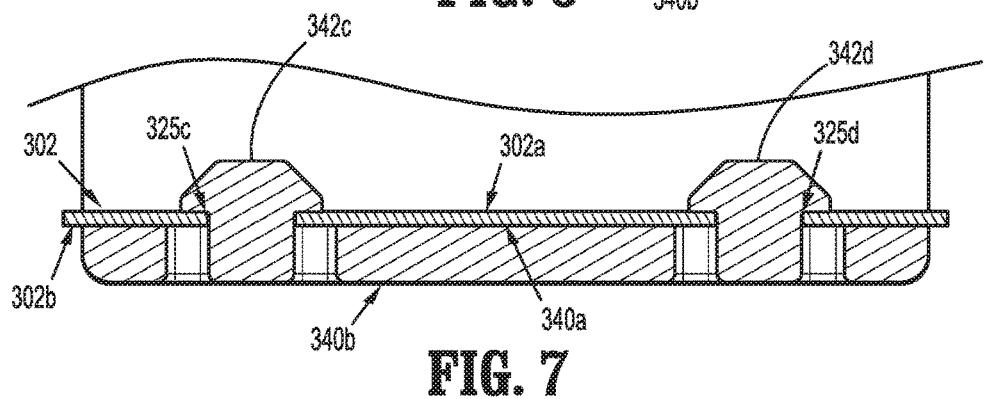
FIG. 7 is a cross sectional view of the drape management assembly taken along the line 7-7 of FIG. 5.

With reference to FIGS. 4-7, the insert 340 of the drape management assembly 300 may be dimensioned such that insert 340 substantially conforms to the grasping portion 320 (e.g., a bottom surface of the lip 320a of the grasping portion 320) of the clip 302. In use, to affix the insert 340 to the clip 302, the top surface 340a of the insert 340 is "pressed" into the bottom surface 302b of the clip 302 such that the flanges 344a-344d of the protrusions 342a-342d of the insert 340 are guided or pressed into the respective slots 325a-325d of the clip 302. Such guiding or pressing of the protrusions 342a-342d of the insert 340 into the slots 325a-325d of the clip 302 resiliently biases the flanges 344a-344d of the protrusions 342a-342d inward (not explicitly shown) until the flanges 344a-344d clear or otherwise overcome the slots 325a-325d of the clip 302 and "snap" into contact with the top surface 302a of the clip 302. Specifically, upon clearing the slots 325a-325d of the clip 302, the clip 302 is coupled between a bottom surface of the flanges 344a-344d of the protrusions 342a-342d of the insert 340 and the top surface 340a of the insert 340, as shown in FIG. 7. In use, the insert 340 may be removed from clip 302 (not explicitly shown) by compressing or biasing the flanges 344a-344d of the protrusions 342a-342d of the insert 340 inward to clear slots 325a-325d of the clip 302.

With reference to FIGS. 4, 8, and 9, drape management assembly 300 includes an elbow 350 interconnecting base portion 310 and grasping portion 320 of clip 302. Elbow 350 functions as a spring to resiliently bias the grasping portion 320 of the clip 302 in a direction "D" (FIG. 9) towards the upper portion 150a of the instrument drive unit 150 of the robotic surgical assembly 100. In this manner, the bottom surface 302b of the grasping portion 320 of the clip 302 (or the bottom surface 340b of the insert 340 if attached to the clip 302) is in contact with the instrument drive unit 150. The resilient bias of the elbow 350 urges the grasping portion 320 in the direction "D" such that the grasping portion 320 of the clip 302 (or the insert 340) adequately affixes, grips, or pins the surgical drape 30 onto or against the surface to which it is in contact with, such as, for example, the upper portion 150a of the instrument drive unit 150. In this configuration, the drape management assembly 300 is in an approximated, gripping position.

To deflect or open the grasping portion 320 of the clip 302 from its default position (FIGS. 2, 3, 5, 8, and 9), a force in the direction "U" (FIG. 9) may be applied to the tab 320b of the grasping portion 320 of the clip 302 to flex or bias the elbow 350 of the clip 302 such that the grasping portion 320 moves away from the surgical drape 30 and the upper portion 150a of the instrument drive unit 150 of the robotic surgical assembly 100 to an unapproximated position (not explicitly shown). In the unapproximated position, the surgical drape 30, or an excess quantity 30a of the surgical drape 30, may be removed from between the cavity or gap 330 of the clip 302 and the instrument drive unit 150. Upon removing the surgical drape 30, a clinician may release the grasping portion 320 of clip 302 upon which, the spring bias of elbow 350 of the clip 302 will cause the drape management assembly 300 to return to its initial approximated position (FIGS. 2, 3, 5, 8, and 9).

In embodiments, the clip 302 of the drape management assembly 300 may be formed of a plastic, steel, stainless steel, sheet metal, or any other suitable material such that the clip 302 is capable of withstanding repeated movements or deflections from an approximated position to an unapproximated position without yielding or deforming. In some embodiments, the clip 302 is plated, e.g., through an electroplating process, with an electroless nickel, bright nickel, chrome, zinc, or the like. In other embodiments, the clip 302 of the drape management assembly 300 may be polished, electropolished, barrel-finished, deburred, or the like, e.g., to smooth out the edges of clip 302, for improved appearance or finish, and corrosion protection, or to inhibit cutting or tearing of surgical drape 30.

In embodiments, the insert 340 of the drape management assembly 300 may be formed of a flexible material configured to conform to the bottom surface 302b of the clip 302 while still being able to provide adequate grip to engage the surgical drape 30. For example, the insert 340 may be formed from silicone, natural rubber, nitrile, urethane, and the like. The insert 340 is more flexible than the clip 302 and may have a durometer of about shore A45 to about shore A55. In some embodiments, the insert 340 may have a durometer of about shore A50.

Figure 10:
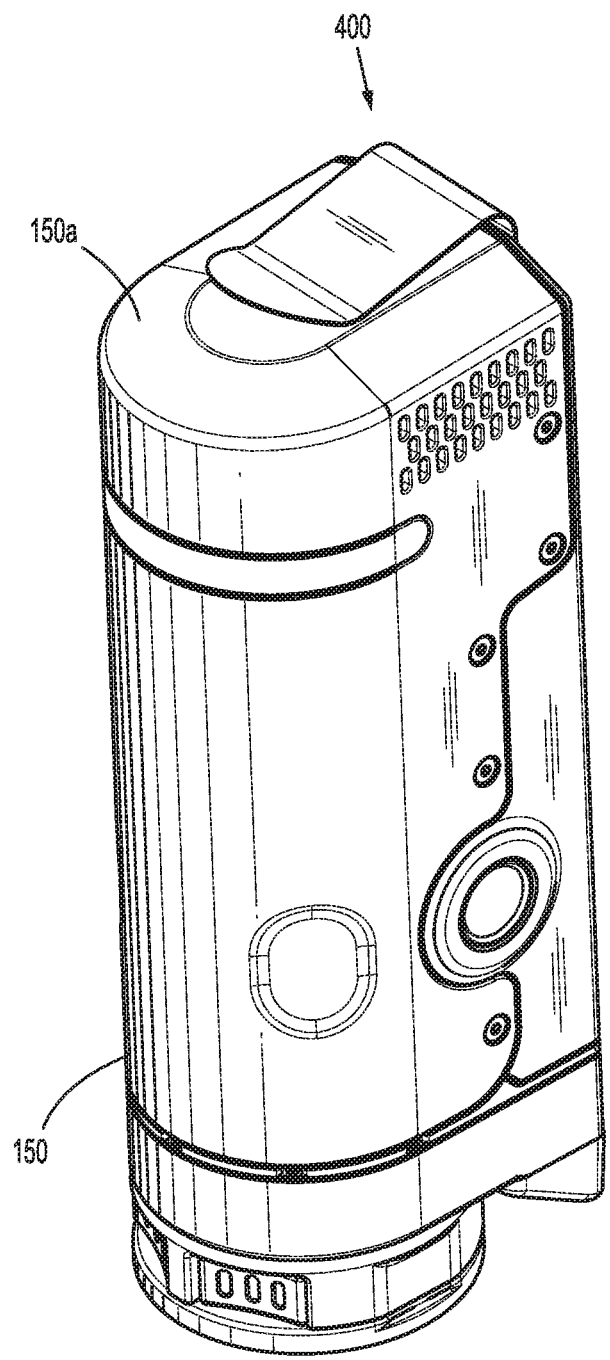
FIG. 10 is a clip in accordance with another embodiment of the present disclosure.

With reference to FIG. 10, a clip 400 is provided in accordance with another embodiment of the present disclosure. Clip 400 may be substantially similar to the embodiment of clip 302 described hereinabove except that clip 400 is not configured for receiving an insert. Therefore, clip 400 may also operate as a device for gripping, pinning, or affixing surgical drape 30 (not explicitly shown) to instrument drive unit 150.

With reference to FIGS. 11 and 12, a clip 500 is provided in accordance with another embodiment of the present disclosure. Clip 500 is substantially similar to the embodiment of clip 302 described above except that clip 500 is specifically configured to be coupled to the slide rail 20 of the robotic arm 2 of the robotic surgical assembly 100 (FIG. 1) rather than the instrument drive unit 150. However, it is contemplated that clip 500 may be attachable to the instrument drive unit 150 (FIG. 2), such as, for example, an upper portion thereof. Due to the substantial similarity between clips 302, 500, only details of clip 500 deemed necessary to elucidate differences from clip 302 will be described in detail.

Clip 500 includes a base portion 510 configured for selective connection to the end portion 20a of the slide rail 20, and a grasping portion 520 extending from the base portion 510 for affixing or pinning the surgical drape 30 (FIG. 9) to the slide rail 20. Base portion 510 of clip 500 is planar and has a curved or bent elbow 550 extending therefrom. The elbow 550 interconnects the base portion 510 and the grasping portion 520. The base portion 510 may be oriented at any suitable angle (e.g., between about 85 and 115 degrees, or between about 90 and 110 degrees) relative to the elbow 550. As such, base portion 510 of clip 500 is substantially perpendicular relative to base portion 310 of clip 302 (FIGS. 2-9).

The base portion 510 of clip 500 defines a pair of apertures (not explicitly shown) therethrough dimensioned for receipt of a pair of fasteners 501, 503 for securing or fixing clip 500 to an outer surface 21 of slide rail 20. In other embodiments, a bottom surface (not explicitly shown) of base portion 510 may have adhesive for securing clip 500 to slide rail 20. When clip 500 is assembled to slide rail 20, clip 500 extends longitudinally along a longitudinal axis defined by slide rail 20, with grasping portion 520 oriented towards end portion 20a of slide rail 20.

Clip 500 may also have an insert 540, similar to insert 340 of FIGS. 2-9, attached to grasping portion 520 for enhancing the ability of grasping portion 520 to hold excess drape 30 between grasping portion 520 and outer surface 21 of slide rail 20.

In use, grasping portion 520 may be moved outwardly relative to base portion 510 about elbow 550 to space grasping portion 520 from outer surface 21 of slide rail 20. With grasping portion 520 spaced from outer surface 21 of slide rail 20, excess drape 30 may be positioned within a cavity 530 cooperatively defined by clip 500 and outer surface 21 of slide rail 20. Upon the cavity 530 receiving excess drape 30, the grasping portion 520 is resiliently biased, via elbow 550, toward outer surface 21 of slide rail 20. As grasping portion 520 moves toward outer surface 21 of slide rail 20, insert 540 engages drape 30 to hold drape 30 against outer surface 21 of slide rail 20, thereby preventing excess drape 30 from exiting cavity 530. In accordance with the present disclosure, it is further contemplated that any clip provided herein may include features or the like, which enhance a gripping and retention of a surgical drape 30 against/to the robotic surgical system. Such features may include and are not limited to ribbing, nubs, coatings, over molding, surface texturing, appliques, and the like.

In embodiments, any clip and/or instrument drive unit 150 provided herein, may include one or more sensors configured to detect the presence of surgical drape 30 between the clip and instrument drive unit 150. The sensors may alert a clinician when surgical drape 30 is initially inserted between the clip and instrument drive unit 150, and/or removed from between the clip and instrument drive unit 150. Such sensors may include, for example, contact sensors, optical sensors, RFID sensors, Ferro-magnetic or magnetic tape sensors, strain gauges, or the like.

In some embodiments, any surface of any clip and/or instrument drive unit 150 provided herein may include an elastomeric material or coating (e.g., a rubberized tape and/or paint) to, for example, increase adhesion with surgical drape 30.

In certain embodiments, any clip provided herein may be a multi-tined clip having a substantially fork-like shape such that surgical drape 30 can, for example, be placed between the tines of the clip to prevent bunching of surgical drape 30, or for individual tines of the clip to deflect by varying amounts in order to accommodate various quantities of surgical drape 30 at various locations along a width of the clip.

It should be understood that the foregoing description is only illustrative of the present disclosure. Various alternatives and modifications can be devised by those skilled in the art without departing from the disclosure. Accordingly, the present disclosure is intended to embrace all such alternatives, modifications, and variances. The embodiments described with reference to the attached drawings are presented only to demonstrate certain examples of the disclosure. Other elements, steps, methods, and techniques that are insubstantially different from those described above and/or in the appended claims are also intended to be within the scope of the disclosure.

The invention claimed is:

1. A robotic surgical assembly, comprising:
   a robotic arm;
   a surgical drape;
   a clip configured to couple the surgical drape to the robotic arm, the clip including:
      a base portion configured for coupling to the robotic arm; and
      a grasping portion extending from the base portion, the base portion and the grasping portion defining a cavity therebetween, wherein the base portion and the grasping portion are arranged to retain a quantity of the surgical drape in the cavity; and
   an insert configured to couple to the clip, the insert including:
      a top surface having a plurality of protrusions extending therefrom, the plurality of protrusions including a plurality of flanges extending from a surface thereof; and
      a frictional bottom surface configured for contact with the surgical drape,
   wherein a plurality of slots are defined through the clip, and wherein the plurality of slots are configured to receive the plurality of protrusions of the insert to couple the insert to the clip.

2. A robotic surgical assembly, comprising:
   a robotic arm;
   a surgical drape;
   a clip configured to couple the surgical drape to the robotic arm, the clip including:
      a base portion configured for coupling to the robotic arm; and
      a grasping portion extending from the base portion, the base portion and the grasping portion defining a cavity therebetween, wherein the base portion and the grasping portion are arranged to retain a quantity of the surgical drape in the cavity; and
   an insert configured to couple to the clip, the insert including:
      a top surface having a plurality of protrusions extending therefrom, the plurality of protrusions including a plurality of flanges extending from a surface thereof; and
      a frictional bottom surface configured for contact with the surgical drape, wherein the surgical drape is configured to enclose the robotic arm, and the clip and the insert are configured to incrementally release an excess quantity of the surgical drape such that the robotic arm maintains a full range of motion while enclosed within the surgical drape.

3. The robotic surgical assembly of claim 2, wherein the excess quantity of the surgical drape is retained between an upper portion of an instrument drive unit and the clip.

4. A robotic surgical assembly, comprising:
   a robotic arm;
   a surgical drape;
   a clip configured to couple the surgical drape to the robotic arm, the clip including:
      a base portion configured for coupling to an instrument drive unit or a slide rail of the robotic arm; and
      a grasping portion extending from the base portion, the base portion and the grasping portion defining a cavity therebetween, wherein the base portion and the grasping portion are arranged to retain a quantity of the surgical drape in the cavity, wherein the clip includes an elbow interconnecting the base portion and the grasping portion, the elbow configured to resiliently bias the grasping portion of the clip to an approximated position towards the instrument drive unit or the slide rail, the slide rail being connected to the robotic arm and the instrument drive unit being connected to the slide rail; and
   an insert configured to couple to the clip, the insert including:
      a top surface having a plurality of protrusions extending therefrom, the plurality of protrusions including a plurality of flanges extending from a surface thereof; and
      a frictional bottom surface configured for contact with the surgical drape.

5. The robotic surgical assembly of claim 4, further comprising a plurality of slots defined through the clip, the plurality of slots configured to receive the plurality of protrusions of the insert to couple the insert to the clip.

6. The robotic surgical assembly of claim 4, wherein the base portion of the clip is coupled to an instrument drive unit or a slide rail, and the grasping portion of the clip is movable between an approximated position and an unapproximated position relative to the instrument drive unit or the slide rail.

7. The robotic surgical assembly of claim 1, wherein the clip is formed from a material selected from the group consisting of plastic, steel, stainless steel, spring steel, and sheet metal.

8. A robotic surgical assembly, comprising:
- a robotic arm;
- a surgical drape;
- a clip configured to couple the surgical drape to the robotic arm, the clip including:
  - a base portion configured for coupling to the robotic arm, wherein the base portion of the clip is coupled to an instrument drive unit or a slide rail; and
  - a grasping portion extending from the base portion, the base portion and the grasping portion defining a cavity therebetween, wherein the base portion and the grasping portion are arranged to retain a quantity of the surgical drape in the cavity, wherein the grasping portion of the clip is movable between an approximated position and an unapproximated position relative to the instrument drive unit or the slide rail; and
- an insert configured to couple to the clip, the insert including:
  - a top surface having a plurality of protrusions extending therefrom, the plurality of protrusions including a plurality of flanges extending from a surface thereof; and
  - a frictional bottom surface configured for contact with the surgical drape.

9. The robotic surgical assembly of claim 8, further comprising a plurality of slots defined through the clip, the plurality of slots configured to receive the plurality of protrusions of the insert to couple the insert to the clip.

10. The robotic surgical assembly of claim 8, wherein the clip includes an elbow interconnecting the base portion and the grasping portion, the elbow configured to resiliently bias the grasping portion of the clip to an approximated position towards an instrument drive unit or a slide rail, the slide rail being connected to the robotic arm and the instrument drive unit being connected to the slide rail.

11. The robotic surgical assembly of claim 1, wherein the clip includes an elbow interconnecting the base portion and the grasping portion, the elbow configured to resiliently bias the grasping portion of the clip to an approximated position towards an instrument drive unit or a slide rail, the slide rail being connected to the robotic arm and the instrument drive unit being connected to the slide rail.

12. The robotic surgical assembly of claim 1, wherein the clip is formed from a material selected from the group consisting of plastic, stainless steel, spring steel, and sheet metal.

13. The robotic surgical assembly of claim 1, wherein the base portion of the clip is coupled to an instrument drive unit or a slide rail, and the grasping portion of the clip is movable between an approximated position and an unapproximated position relative to the instrument drive unit or the slide rail.

* * * * *